US010794990B2

(12) United States Patent
Takamine et al.

(10) Patent No.: US 10,794,990 B2
(45) Date of Patent: Oct. 6, 2020

(54) STRUCTURE EVALUATION APPARATUS, STRUCTURE EVALUATION SYSTEM, AND STRUCTURE EVALUATION METHOD

(71) Applicants: Kabushiki Kaisha Toshiba, Tokyo (JP); Kyoto University, Kyoto (JP)

(72) Inventors: Hidefumi Takamine, Tokyo (JP); Kazuo Watabe, Kanagawa (JP); Tomoki Shiotani, Kyoto (JP)

(73) Assignees: Kabushiki Kaisha Toshiba, Tokyo (JP); Kyoto University, Kyoto (JP)

( * ) Notice: Subject to any disclaimer, the term of this patent is extended or adjusted under 35 U.S.C. 154(b) by 270 days.

(21) Appl. No.: 15/454,316

(22) Filed: Mar. 9, 2017

(65) Prior Publication Data
US 2017/0269204 A1 Sep. 21, 2017

(30) Foreign Application Priority Data

Mar. 16, 2016 (JP) .................................. 2016-052944

(51) Int. Cl.
*G01S 7/06* (2006.01)
*G01N 17/00* (2006.01)
(Continued)

(52) U.S. Cl.
CPC ............... *G01S 7/06* (2013.01); *G01N 17/00* (2013.01); *G01N 33/383* (2013.01); *G01S 13/88* (2013.01)

(58) Field of Classification Search
CPC .......... G01S 7/06; G01S 13/88; G01S 13/885; G01S 13/887; G01S 13/888; G01N 17/00;
(Continued)

(56) References Cited

U.S. PATENT DOCUMENTS 6,246,354 B1 * 6/2001 Liedtke ............... G01S 13/0209
342/196
6,429,802 B1 * 8/2002 Roberts ................... G01V 3/12
342/175
(Continued)

FOREIGN PATENT DOCUMENTS

JP      2001-165870 A     6/2001
JP      2005-331404 A    12/2005
(Continued)

OTHER PUBLICATIONS

"The 8$^{th}$ Caesar Lecture", Public Works Research Institute, Aug. 28, 2015, pp. 55 and 102 with cover page (with unedited computer generated English translation).

*Primary Examiner* — Timothy A Brainard
*Assistant Examiner* — Michael W Justice
(74) *Attorney, Agent, or Firm* — Oblon, McClelland, Maier & Neustadt, L.L.P.

(57) ABSTRACT

A structure evaluation apparatus has an acquisitor and an evaluator. The acquisitor acquires a distribution that represents a distribution of strength of a reflected wave obtained by an electromagnetic radar scan to a reinforced concrete which comprises concrete and a material other than concrete. The evaluator calculates similarity, with reference to a reference region including the material in the distribution, of other regions including the material than the reference region in the distribution.

7 Claims, 5 Drawing Sheets

(51) Int. Cl.
*G01N 33/38* (2006.01)
*G01S 13/88* (2006.01)

(58) Field of Classification Search
CPC ...... G01N 33/383; C04B 14/06; C04B 28/02; B22F 3/1055; B22F 2999/00
See application file for complete search history.

(56) References Cited

U.S. PATENT DOCUMENTS

| | | | | |
|---|---|---|---|---|
| 8,306,747 | B1* | 11/2012 | Gagarin | G01C 7/04 |
| | | | | 701/408 |
| 9,194,819 | B2* | 11/2015 | Bulumulla | G01M 7/04 |
| 2003/0076254 | A1* | 4/2003 | Witten | G01S 7/28 |
| | | | | 342/22 |
| 2012/0280849 | A1* | 11/2012 | Chang | G01V 3/12 |
| | | | | 342/22 |
| 2013/0082866 | A1* | 4/2013 | Jaganathan | G01S 13/88 |
| | | | | 342/22 |
| 2014/0368373 | A1* | 12/2014 | Crain | G01S 5/02 |
| | | | | 342/5 |
| 2015/0115980 | A1* | 4/2015 | Bulumulla | G01M 7/04 |
| | | | | 324/642 |
| 2015/0362422 | A1* | 12/2015 | Mazzeo | G01N 27/20 |
| | | | | 324/238 |

FOREIGN PATENT DOCUMENTS

| | | |
|---|---|---|
| JP | 2008-39429 A | 2/2008 |
| JP | 2008-76386 A | 4/2008 |

* cited by examiner

STRUCTURE EVALUATION APPARATUS, STRUCTURE EVALUATION SYSTEM, AND STRUCTURE EVALUATION METHOD

CROSS-REFERENCE TO RELATED APPLICATION

This application is based upon and claims the benefit of priority from Japanese Patent Application No. 2016-052944, filed Mar. 16, 2016; the entire contents of which are incorporated herein by reference.

BACKGROUND

Field of Art

Embodiments of the present invention relate to a structure evaluation apparatus, a structure evaluation system, and a structure evaluation method.

Related Art

Japanese Patent Application Publication No. 2005-331404 discloses the non-destructive testing of reinforced concrete structures (hereinafter, "reinforced concrete"), wherein the electromagnetic radar method has been used. In electromagnetic radar method, an electromagnetic radar apparatus radiates reinforced concrete with an electromagnetic pulse and detects the electromagnetic waves reflected from rebars and gaps inside the reinforced concrete. From the characteristics of the reflected waves, it is possible to detect the position of rebars and anomalies such as gaps inside the reinforced concrete. However, in diagnosing the conventional electromagnetic radar measurement results of reinforced concrete, there has been great reliance on experience and intuition. For that reason, there have been cases in which it is not possible to make a stable quantitative evaluation of sturdiness. This type of problem is not limited to steel-reinforced concrete, but is common to all reinforced concrete.

DESCRIPTIONS OF EMBODIMENT

A structure evaluation apparatus, a structure evaluation system, and a structure evaluation method of embodiments will be described below, with references made to drawings.

Figure 1:
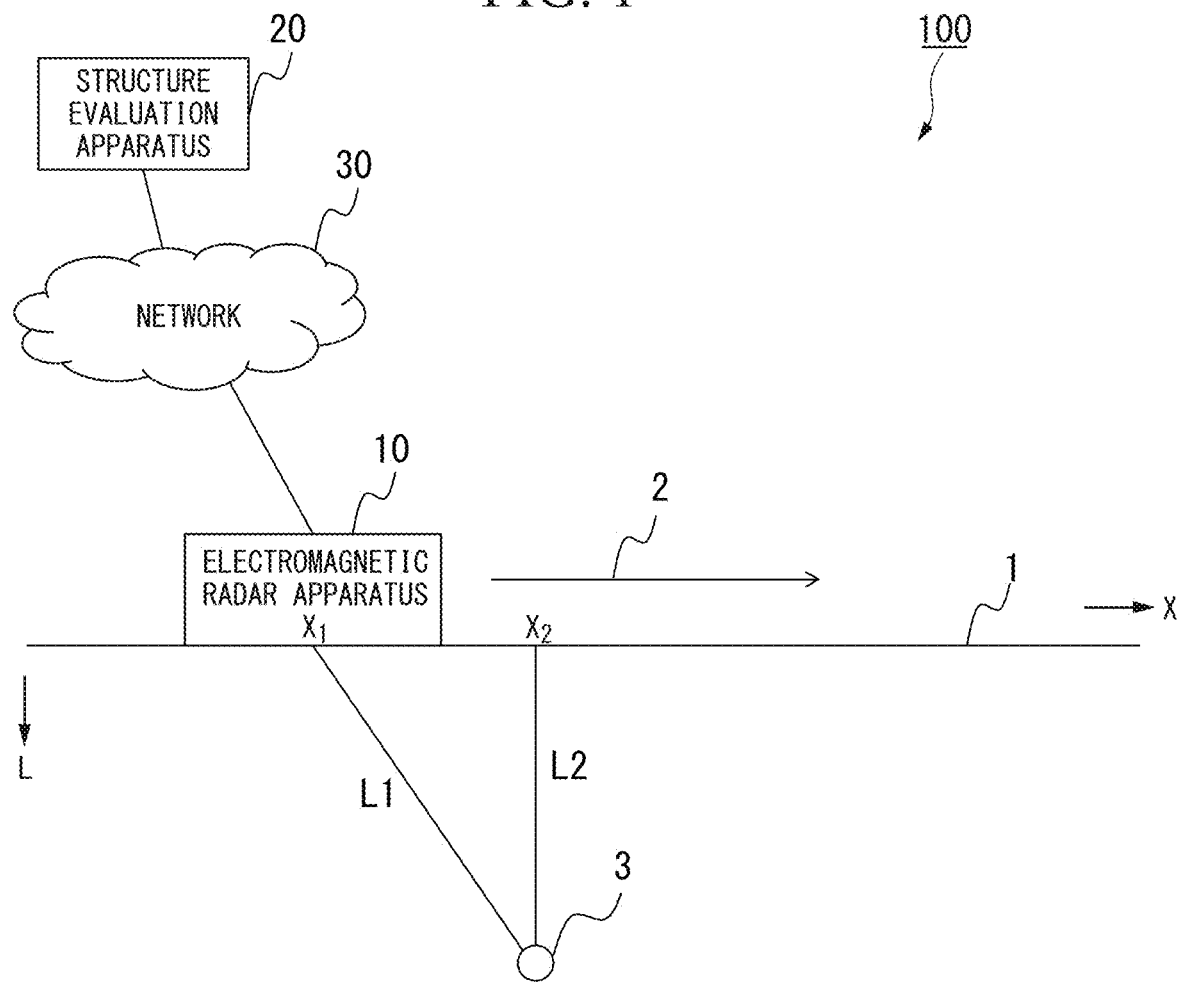
FIG. 1 shows the system constitution of a structure evaluation system 100 of an embodiment.

FIG. 1 shows the system constitution of the structure evaluation system 100 of an embodiment. The structure evaluation system 100 has an electromagnetic radar apparatus 10 and a structure evaluation apparatus 20. The electromagnetic radar apparatus 10 and the structure evaluation apparatus 20 are connected via a network 30 so as to be able to communicate. The network 30 can be of any constitution, and may be constituted using, for example, the Internet.

The electromagnetic radar apparatus 10 scans the surface of the reinforced concrete 1 in the direction of the arrow 2 and detects the rebar 3 inside the reinforced concrete 1. The electromagnetic radar apparatus 10 transmits a distribution of color attribute obtained from the detection results to the structure evaluation apparatus 20. The distribution of color attribute represents that represents the strength of the reflected waves by tone density, hereinafter referred to as a gray scale image. The reinforced concrete 1 is constituted by concrete and rebars. The rebars are made of a material having a different permittivity than concrete.

The structure evaluation apparatus 20, based on the gray scale image obtained from the electromagnetic 10, evaluates the damageless regarding deterioration or the like of the reinforced concrete 1.

Next, the specific construction of the electromagnetic radar apparatus 10 will be described. The electromagnetic radar apparatus 10 has an electromagnetic transmitter, a receiver, an analyzer, and a communicator. The electromagnetic transmitter transmits an electromagnetic pulse to the surface of the reinforced concrete 1. The receiver receives the electromagnetic waves reflected back through the inside of the reinforced concrete 1. When this occurs, if an anomaly (such as a rebar) having a permittivity that is difference from that of concrete exists inside the reinforced concrete 1, the electromagnetic pulse is reflected at that position and returns to the electromagnetic radar apparatus 10. A reflected wave responsive to the condition of the anomaly within the reinforced concrete 1 is therefore obtained at the receiver.

Figure 2:
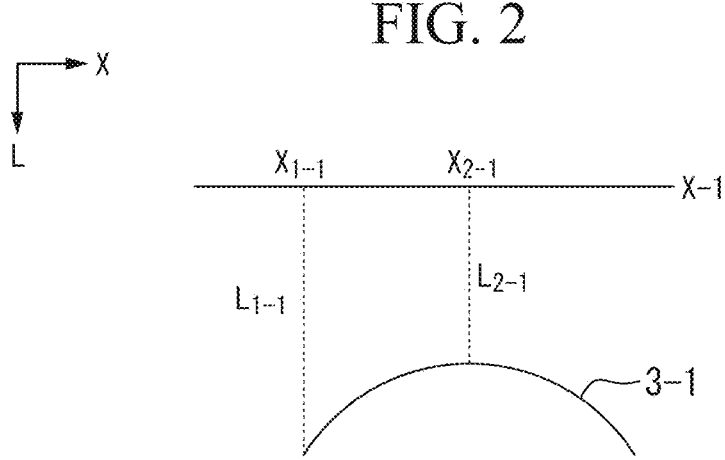
FIG. 2 shows the distance relationship between the point of transmission of an electromagnetic pulse and a rebar.

For example, if there is a rebar 3 inside the reinforced concrete 1, as shown in FIG. 1, the electromagnetic pulse is reflected with high intensity at the internal rebar 3, and returns to the electromagnetic radar apparatus 10. The electromagnetic radar apparatus 10 can calculate the distance between the point of transmission of the electromagnetic pulse and rebar 3 from the time until the strong reflected wave returns. Accompanying the scanning by the electromagnetic radar apparatus 10, the distance between the point of transmission of the electromagnetic pulse and rebar 3 successively changes such as from L1 to L2 in a sequential order. The change in the distance between the point of transmission of the electromagnetic pulse and rebar 3 can be represented as shown in FIG. 2, which shows the distance relationship between the point of transmission of the electromagnetic pulse and rebar. As shown in FIG. 2, the rebar exhibiting the strong reflected wave appears as an arc pattern 3-1.

Returning to the description of the electromagnetic radar apparatus 10, the analyzer analyzes the reflected wave obtained by the receiver and, based on the intensity of the reflected wave, generates a gray scale image. The communicator transmits the generated gray scale image to the structure evaluation apparatus 20.

Figure 3:
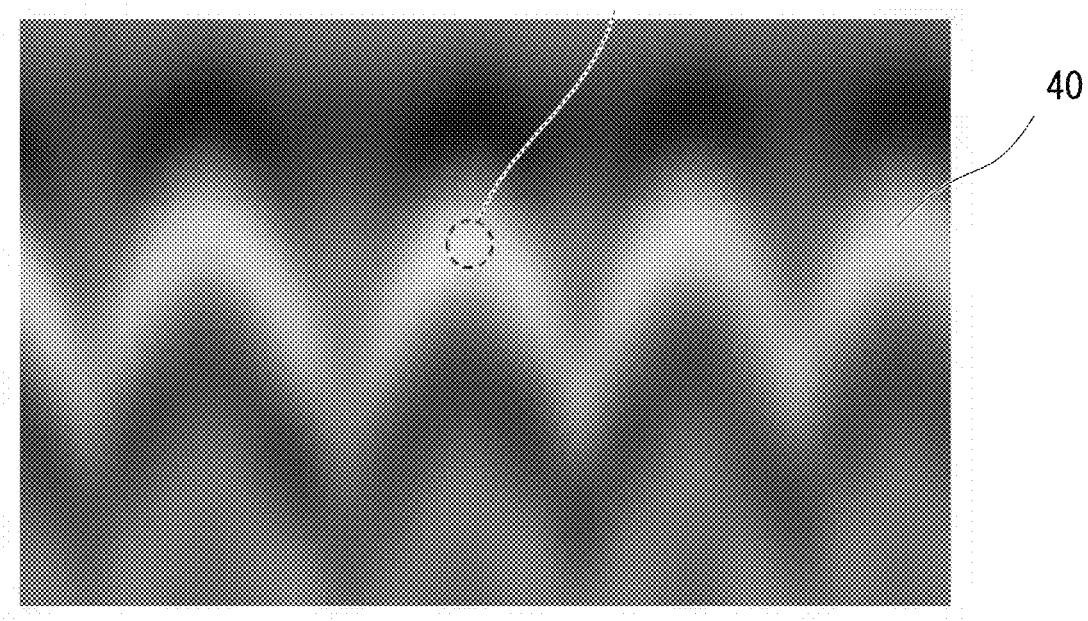
FIG. 3 shows a specific example of a gray scale image when the surface of actual reinforced concrete 1 is scanned.

FIG. 3 shows a specific example of a gray scale image. FIG. 3 shows a specific example of a gray scale image when the actual surface of the reinforced concrete 1 is scanned. In FIG. 3, the arc pattern 40 in accordance with the row of rebars can be seen. The position on one rebar is shown by the dotted line 41. As shown in FIG. 3, because the permittivity of rebars is larger than that of concrete, the arc pattern 40 is displayed white. In contrast, in an unsound reinforced concrete 1, in addition to gaps existing near the rebars caused by fault fabrication, expansion and cracking caused by corrosion of the rebars occur. If a gap exists inside the reinforced concrete 1, because the permittivity of air is smaller than that of concrete, the phase of the reflected wave is inverted, causing a reflected wave pattern in which the tone densities are the reverse of the rebar. That is, if there is a gap in the reinforced concrete 1, the region of the gap is displayed black.

Expansion of the rebars or cracking in the surrounding area will also influence the behavior of the electromagnetic waves. Therefore, a change is seen in the pattern of reflected waves received at the electromagnetic radar apparatus 10. For that reason, in terms of the principle, from the gray scale image obtained by the electromagnetic radar measurement, it is thought that a worker judges whether or not there is a defect inside the reinforced concrete 1, and makes an evaluation of damageless. However, in an actual gray scale image, it is generally difficult to distinguish clearly the change in the distribution reflecting the change in the condition of the reinforced concrete 1, and in diagnosing for damageless and the like, there has been great reliance on intuition and experience of a technician. A specific method for solving this problem is described below.

Figure 4:
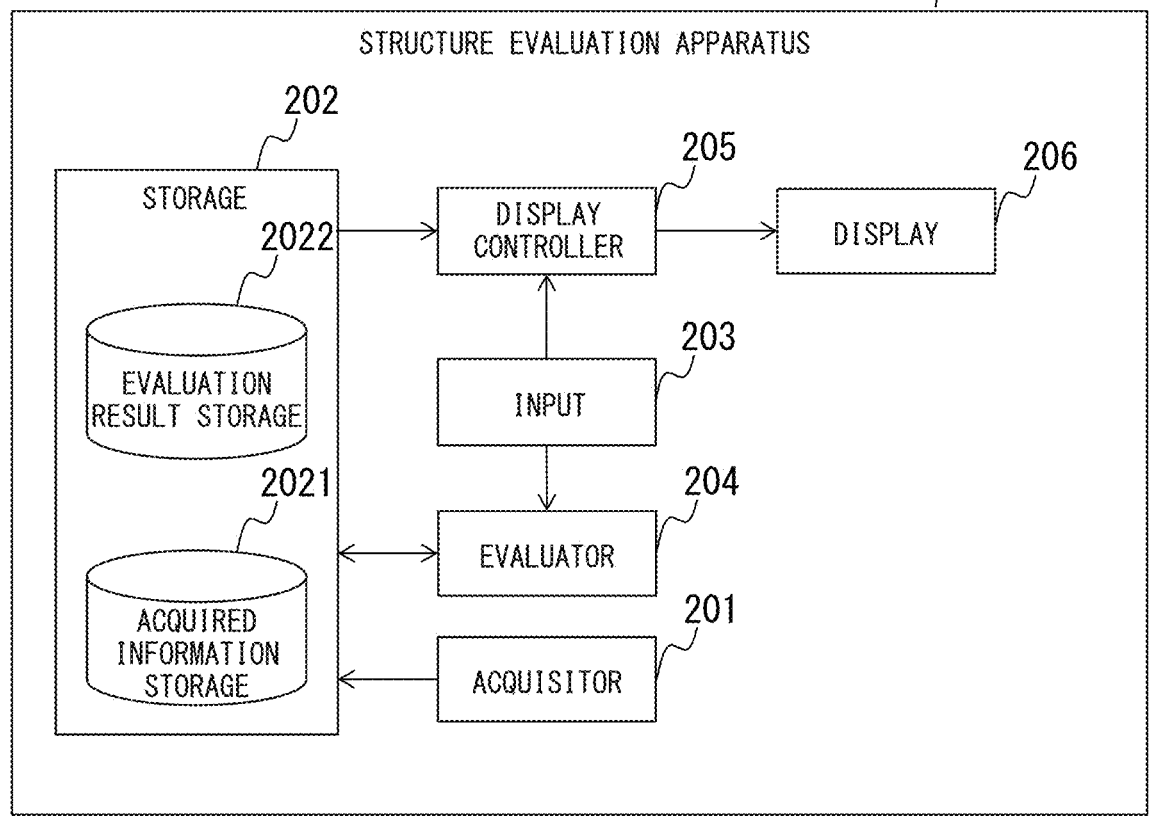
FIG. 4 is a simplified block diagram showing the functional constitution of a structure evaluation apparatus 20.

FIG. 4 is a simplified block diagram showing the functional constitution of the structure evaluation apparatus 20 has a CPU (central processing unit) and a memory or auxiliary storage device connected by a bus, and executes an evaluation program. By executing the evaluation program, the structure evaluation apparatus 20 functions as an acquisitor 201, a storage 202, an input 203, an evaluator 204, a display controller 205, and a display 206. All or a part of the functions of the structure evaluation apparatus 20 may be implemented using hardware such as an ASIC (application-specific integrated circuit), a PLD (programmable logic device), or a FPGA (field-programmable gate array). The evaluation program may be recorded in a computer-readable recording medium. A computer-readable recording medium is a removable medium such as a flexible disk, a magneto-optical disk, a ROM, or a CD-ROM, or a storage device such as a hard-disk built into a computer system. Also, the evaluation program may be transmitted and received via an electrical communication circuit.

The acquisitor 201 acquires a gray scale image from the electromagnetic radar apparatus 10. The acquisitor 201 stores the acquired gray scale image into the storage 202. The storage 202 is constituted by an acquired information storage 2021 and an evaluation result storage 2022. The acquired information storage 2021 is constituted by a storage device such as a magnetic hard disk device or a semiconductor storage device. The acquired information storage 2021 stores information acquired by the acquisitor 201. The acquired information storage 2021 stores, for example, a gray scale image. The evaluation result storage 2022 is constituted by a storage device such as a magnetic hard disk device or a semiconductor storage device. The evaluation result storage 2022 stores the results of the evaluation of a structure by the evaluator 204.

The input 203 is constituted using an existing input device such as a keyboard, a pointing device (for example, a mouse or tablet), a touch panel, or a button. The input 203 is operated by a user when inputting user instructions to the structure evaluation apparatus 20. The input 203 may be an interface for the purpose of connecting an input device to the structure evaluation apparatus 20, in which case the input 203 inputs to the structure evaluation apparatus 20 an input signal generated in response to a user input at the input device.

The evaluator 204 evaluates a structure, based on the gray scale image stored in the acquired information storage 2021. Specifically, the evaluator 204 evaluates a structure by determining the degree of similarity between a sound region in the gray scale image (hereinafter "reference region") and another region. In this case a sound region is a region that includes a rebar and also is as free as possible from gaps and expansion and cracking due to rebar corrosion. In the present embodiment, the correlation is used to calculate the degree of similarity. The specific processing by the evaluator 204 will be described later.

The display controller 205 controls the display of the display 206. The display controller 205 displays on the display 206 a gray scale image stored in the acquired information storage 2021. The display controller 205 also generates a correlation distribution based on the evaluation results and the gray scale image and displays the generated correlation distribution on the display 206. In the present embodiment, the correlation distribution is a contour plot.

The display 206 is an image display device such as a liquid-crystal display or an organic EL (electroluminescence) display. The display 206 displays the gray scale image and the correlation distribution, under control from the display controller 205. The display 206 may be an interface for connecting an image display device to the structure evaluation apparatus 20, in which case the display 206 generates an image signal for displaying the gray scale image and the correlation distribution and outputs the image signal to the image display device to which it is connected.

The processing by the structure evaluation apparatus 20 will now be described, using FIG. 5 to FIG. 9B.

Figure 5:
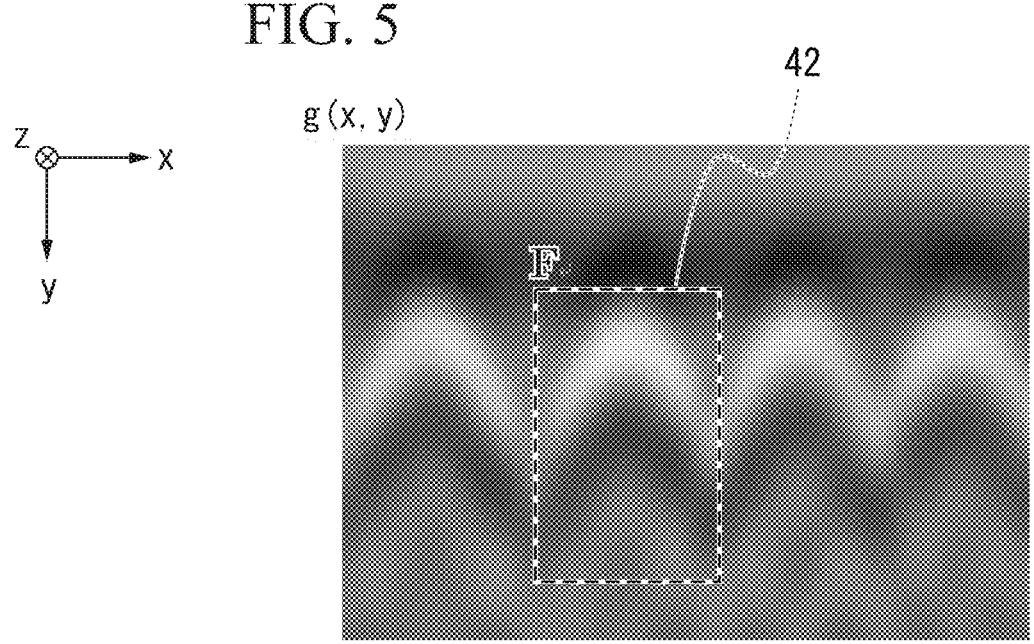
FIG. 5 is a gray scale image used for describing processing.

FIG. 5 is a gray scale image used for describing the processing. In FIG. 5, with x taken as the scanning direction of the electromagnetic radar apparatus 10 and y taken as the depth direction of the reinforced concrete 1, in the gray scale image the cross-sections of the rebars extending in the Z direction are observed. For example, if four rebars extending in the Z direction are cut laterally at the time of scanning, the gray scale image of the xy cross-sections are obtained, as shown in FIG. 5. In FIG. 5, a pattern of four white arcs of the rebars are shown to be connected. This gray scale image will be taken as g(x, y).

Next, a worker selects one rebar that is thought to be sound from the gray scale image g(x, y). In making the selection, for example, the method used is that of selecting one that has high reliability from among the ones that are determined to be sound in accordance with, for example, testing as is conventionally done. Specifically, a worker operates the input 203 to select a rebar that is judged to be sound from the gray scale image g(x, y) displayed on the display 206. The evaluator 204 extracts a certain region of the distribution in the vicinity of the selected rebar. For example, the evaluator 204 extracts the region 42 from the gray scale image g(x, y). In the description to follow, the extracted region 42 will be referred to as the reference region F. The reference region F is desirably selected so as to include as much of the gray scale image that is characteristic of the vicinity of the rebar. The gray scale image of the reference region F will be taken as f(x, y). A characteristic gray scale image of the rebar vicinity is one that has a white arc pattern indicating the rebar.

Next, the evaluator 204 calculates the correlation between the gray scale image f(x, y) and the gray scale image g(x, y). As noted above, a difference occurs in the gray scale image between a sound rebar vicinity and an unsound rebar vicinity. It is thought that the greater is the deterioration in the vicinity of a rebar, the greater it will differ from the gray scale image of the original sound condition. For that reason, the degree of similarity in gray scale image to the reference region F that is thought to be sound serves as an index of the damageless of another region. The correlation C indicating the degree of similarity between the gray scale image f(x, y) and the gray scale image g(x, y) is calculated, for example, by Equation (1).

[Equation 1]

$$C(i, j) = \int\int_{(x,y) \in F} f(x, y) g(x+i, y+j)  \quad \text{(Equation 1)}$$

Figure 6A:
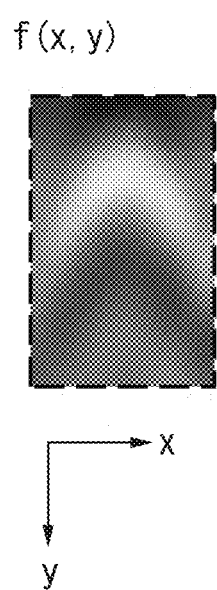
FIGS. 6A and 6B are drawings for describing the method of calculating the correlation.
Figure 6B:
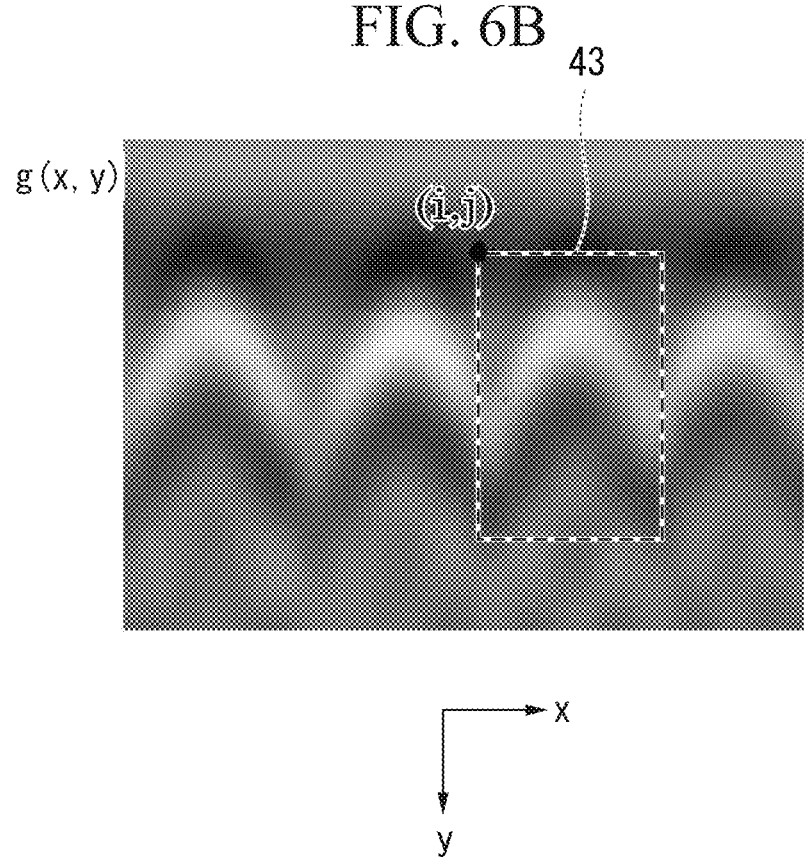

In the above, C(i, j) indicates the correlation at a point (i, j). As shown in FIGS. 6A and 6B, with respect to each rebar, using a point (i, j) as a reference, the product of the region of the gray scale image g(x, y) similar to the reference region F and the gray scale image f(x, y) is integrated within the region. In general, this value is larger, the closer the gray scale image g(x, y) is to the gray scale image f(x, y). Therefore, a region in the vicinity of a rebar included in the target distribution in which value of the calculated C(i, j) is large is similar to the distribution in the vicinity of a sound rebar, and can be treated as being a sound region.

However, the correlation C(i, j) value decreases even if there is an offset between the position of a rebar in the region in which the point (i, j) is used as the reference and the position of a rebar in the reference region F. Because there is a certain degree of variation in the displacement of the rebars, it is difficult to mechanically set the point (i, j) accurately with respect to each rebar. For that reason, rather than simply making a one-to-one setting of the points (i, j) taken as the references with respect to the rebars, it is desirable to calculate the correlation distribution over some range, with some width in the x and y directions. The value of correlation takes the maximum value of Cmax of the correlation distribution at the point at which the position of the rebar in target region coincides with the position of the rebar in the reference region F. Given this, the evaluator 204 adopts the Cmax of each of the target regions in the target distribution g(x, y) as the correlation of the target region. In calculating the correlation, because the magnitude of the measured value (brightness of the region) influences the correlation, it is desirable to normalize using the brightness or normal value in the target region. This is to suppress variation in the correlation due to the brightness.

By the above calculation, the value of correlation to the reference region is obtained for each target region.

Figure 7:
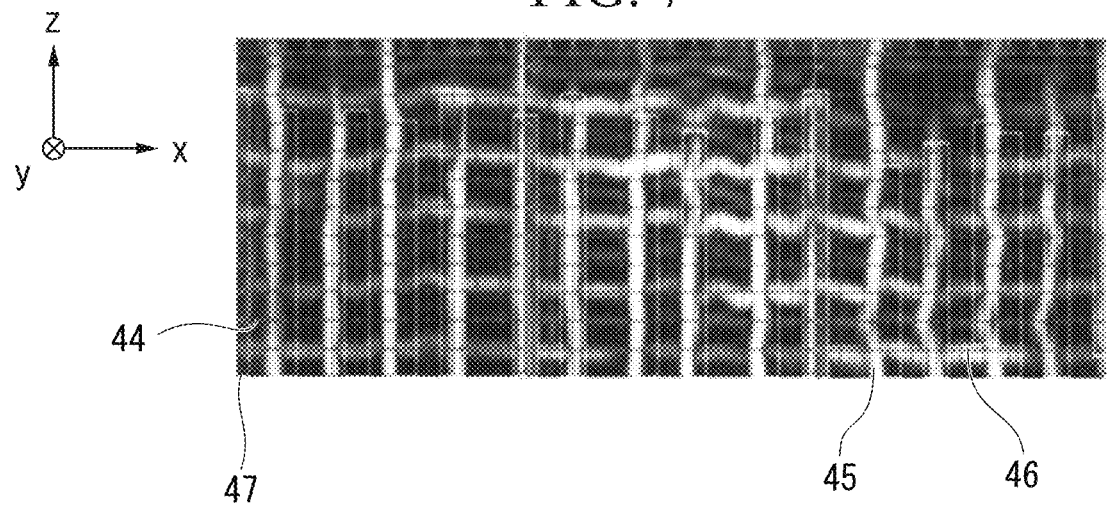
FIG. 7 shows an example of a reinforced concrete floor slab measured using a conventional electromagnetic radar method.

FIG. 7 shows an example of a reinforced concrete floor slab measured by a conventional electromagnetic radar method. FIG. 7 is a view from the bottom surface of the floor slab, in which the scanning lines 44 of the electromagnetic radar are shown in matrix arrangement. The scanning pitch is 5 cm, and a gray scale image of a cross-section is obtained for each scanning line 44. The disposition of the rebars verified from the cross-sections is displayed as a white matrix. The disposition of the rebars is such that main rebars 45 in the z direction are placed at shallow positions (with a covering thickness of up to 3 cm), with force-distributing rebars 46 in the x direction to the rear thereof (with a covering thickness of up to 6 cm).

The square frame 47 that is displayed overlapped with the rebars in the drawing indicates the diagnosis results of the conventional method. Specifically, the frame 47 shows the locations at which the diagnosis results indicate a suspicion of a gap existing. Taking note of the main rebars 45 in FIG. 7, the diagnosis result is that there it is suspected that there exist gaps in the entire region. However, there can be an invisible, almost invisible, or unclearly visible difference between a cross-section of a location diagnosed as having a gape and a cross-section of a location diagnosed as being sound, so that the diagnosis relies greatly on the experience of a technician. For that reason, there are cases in which there is no quantization and reliability is poor. In contrast, in the present embodiment, by calculating the correlation as noted above, a quantitative value can be obtained for each rebar.

Figure 8:
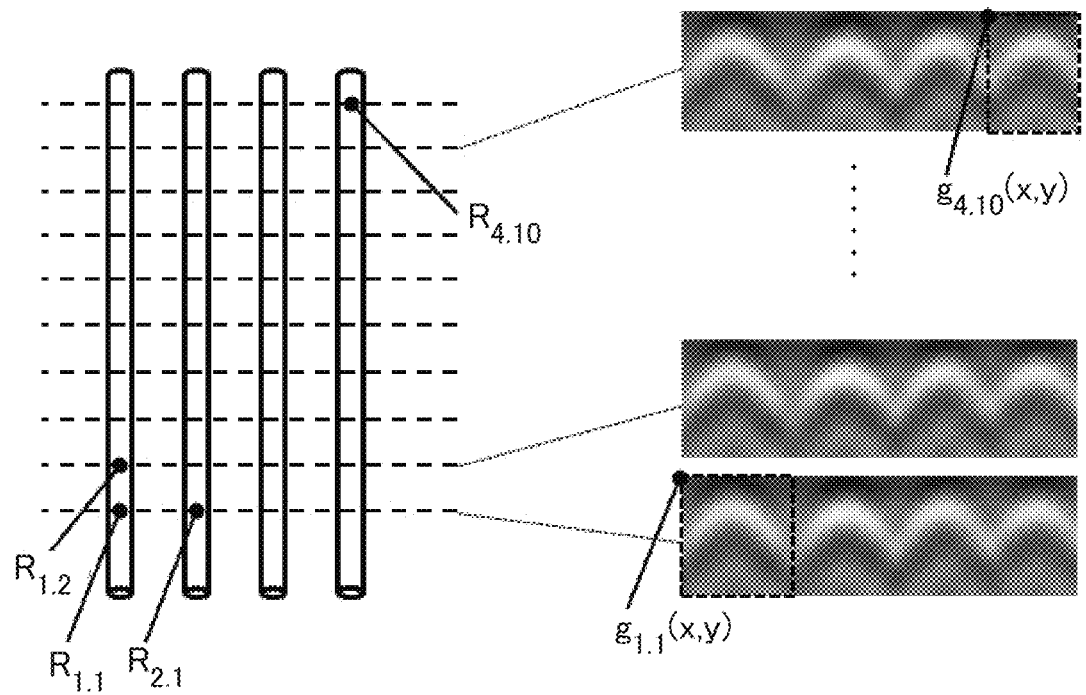
FIG. 8 is a drawing for more-specifically describing an evaluator 204.

FIG. 8 is a drawing for more-specifically describing the evaluator 204. The dashed lines shown in FIG. 8 show the scanning lines of the electromagnetic radar apparatus 10. The correlation is calculated at each position at which a scan line of the electromagnetic radar apparatus 10 cuts across a rebar. For example, at the intersection point R1,1 between the electromagnetic radar apparatus 10 scanning line and the rebar, the cross-sectional gray scale image g1,1 (x, y) is obtained. By calculating the correlation between this g1,1 (x, y) and the reference region F gray scale image f(x, y), the evaluator 204 evaluates the point R1,1. By repeating this processing for each intersection point, the evaluator 204 obtains the correlation for the entire measured region. In the case of FIG. 8, the correlation for the 40 points from the intersection point R1,1 to R4,10 is calculated.

Figure 9A:
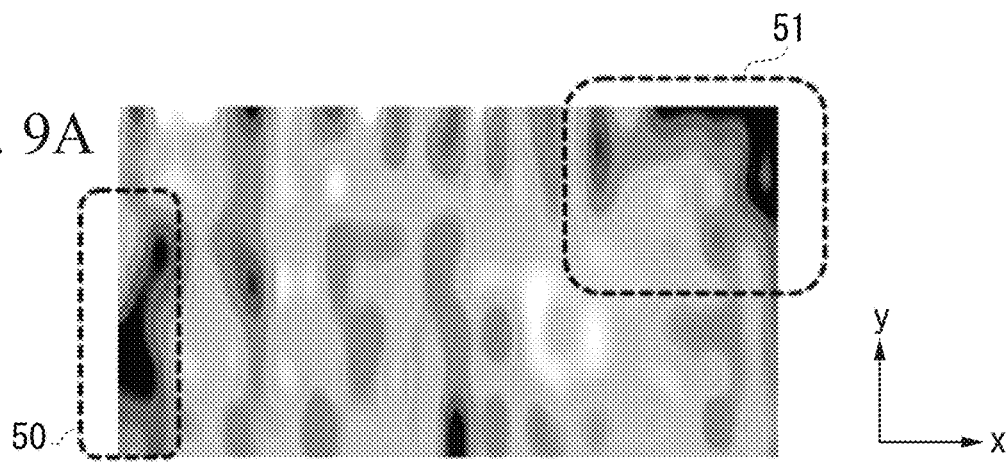
FIGS. 9A and 9B show the output results.

The display controller 205, based on the correlation calculated by the evaluator 204 and the gray scale image, generates a contour plot such as shown in FIG. 9A, by displaying the correlation distribution adjusted to the rebar dispositions. FIG. 9A represents the correlation distribution calculated with respect to the main rebar in the measurement region of FIG. 7. In each of FIGS. 9A and 9B, the lower is the correlation, the blacker is the display, and the higher is the correlation, the whiter is the display. In FIG. 9A, the parts having a high density (parts close to black) have a low correlation, that is, represent a large difference from a sound region. In FIG. 9A, parts in which the density is high, such as the region 50 and a wide range within the region 51 appear. In contrast, in FIG. 9A the parts having low density (parts close to white) have a high correlation, that is, represent a small difference from a sound region. By making a display such as shown in FIG. 9A, the structure evaluation apparatus 20 provides quantitative evaluation results that are visually and intuitive easy to understand. Specifically, the structure evaluation apparatus 20 provides an evaluation result of a high possibility of deterioration occurring in the vicinity of a rebar shown with a high tone density and an evaluation result of a low possibility of deterioration occurring in the vicinity of a rebar shown with a low tone density.

Figure 9B:
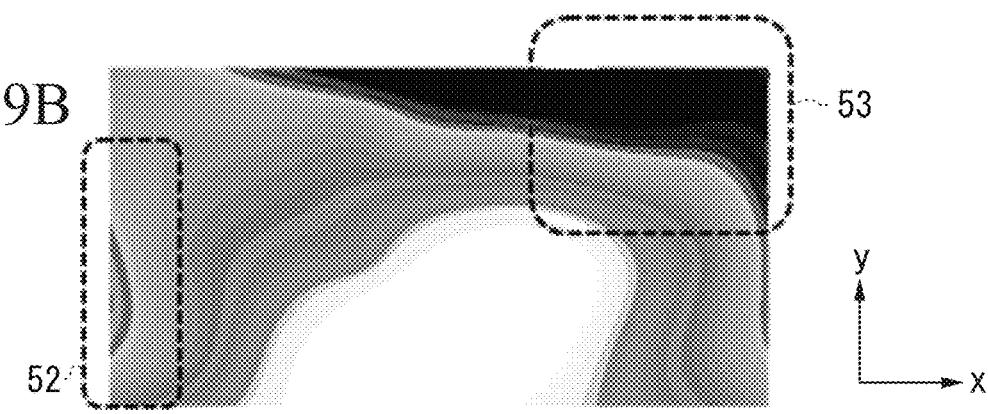

FIG. 9B shows the result for the same region as FIG. 9A using the AE (acoustic emission) tomography method. Whereas FIG. 9A represents the correlation distribution of the main rebars 45 positioned at a depth of approximately 3 to 6 cm from the surface of the reinforced concrete 1, FIG. 9B is the AE tomography result at a depth of 5 cm from the surface of the reinforced concrete 1. In this case, the AE tomography method is a non-destructive testing method using acoustic emissions, which are elastic waves occurring when, for example, a material fails. Acoustic emissions occurring from inside the reinforced concrete 1 are detected by a plurality of acoustic emission sensors disposed on the surface of the reinforced concrete 1, and the distribution of the velocity of travel of the acoustic emissions from the source thereof through the inside of the reinforced concrete 1 is calculated from the plurality of obtained acoustic emission signals. Because the more deteriorated the concrete is, the more the velocity of the acoustic emissions travelling therewithin decreases, the degree of deterioration inside the concrete can be evaluated from the acoustic emission velocity distribution.

Comparing FIG. 9A with FIG. 9B, the upper-right part and lower-left part of the measured region have a high tone density in both. That is, this indicates that there is a possibility that deterioration has occurred in the upper-right and lower-left parts of the measured region. In this manner, the results in FIG. 9A can be predicted as indicating an acceptable evaluation result.

Figure 10:
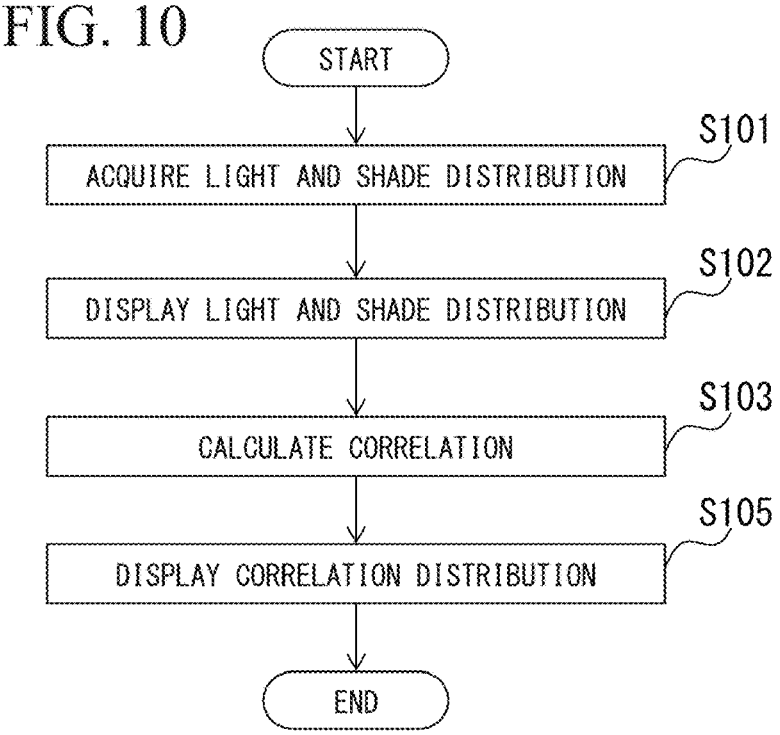
FIG. 10 is a flowchart showing the flow of processing by the structure evaluation apparatus 20.

FIG. 10 is a flowchart showing the flow of processing by the structure evaluation apparatus 20. The acquisitor 201 acquires a gray scale image from the electromagnetic radar apparatus 10 (step S101). The acquisitor 201 stores the acquired gray scale image into the acquired information storage 2021. The user operates the input 203 to input an instruction to display the gray scale image. By this instruction, the display controller 205 causes the display 206 to display the gray scale image stored in the acquired information storage 2021. The display 206 displays the gray scale image under control from the display controller 205 (step S102). Next, the user operates the input 203 to select the reference region in the gray scale image. By this instruction, the evaluator 204 calculates the correlation between the selected reference region and another region in the gray scale image (step S103). The evaluator 204 stores the calculated correlation as the evaluation result into the evaluation result storage 2022. The display controller 205 generates a correlation distribution, based on the gray scale image stored in the acquired information storage 2021 and the evaluation result stored in the evaluation result storage 2022. The display controller 205 controls the display 206 to cause it to display the generated correlation distribution of the display 206. The display 206 displays the correlation distribution under the control of the display controller 205 (step S105).

A structure evaluation apparatus 20 constituted as noted above can stably evaluate the damageless of a structure. Specifically, the structure evaluation apparatus 20 calculates the correlation regarding a gray scale image obtained from the electromagnetic radar apparatus 10 between a reference region that includes a sound rebar and another region. The correlation to the reference region that includes a sound rebar can be thought of as being proportional to the damageless in that region. For that reason, the structure evaluation apparatus 20 can stably evaluate the damageless of a structure by calculating the correlation between a reference region and another region in a gray scale image.

The structure evaluation apparatus 20 generates a correlation distribution based on the evaluation result, which is the result of calculating the correlation, and the gray scale image, and displays the generated correlation distribution. In the correlation distribution, the distribution in accordance with the correlation is shown by tone density. A worker or administrator can look at this display to easy grasp a location at which there is a possibility that deterioration has occurred.

In calculating the correlation, the structure evaluation apparatus 20 uses Cmax in each target region in the target distribution g(x, y) as the correlation of each target region. This enables accurate calculation of the correlation, eliminating the influence of positional offset of the rebars.

Variation examples of the structure evaluation apparatus 20 will now be described.

Although in the present embodiment the constitution has been shown in which the structure evaluation apparatus 20 evaluates the damageless of reinforced concrete, there is no need for this restriction. For example, the structure evaluation apparatus 20 may evaluate the damageless of reinforced concrete other than steel-reinforced concrete. Prestressed concrete (PC) can be cited as a reinforced concrete other than steel-reinforced concrete.

Although in the present embodiment has been shown in which the structure evaluation apparatus 20 displays a gray scale image in response to a user operation, there is no need for this restriction. The constitution may be made such that the structure evaluation apparatus 20 displays each time a gray scale image is acquired from the electromagnetic radar apparatus 10.

The constitution may be made such that the electromagnetic radar apparatus 10 and the structure evaluation apparatus 20 are integrated as one.

The method of determining the degree of similarity need not be restricted to the above-noted correlation. For example, a difference value obtained by the difference between the reference region and the target region may be used as the method for determining the degree of similarity, in which case the smaller is the difference value the smaller the structure evaluation apparatus 20 evaluates the difference to be.

The constitution may be made such that the display controller 205 causes display of the gray scale image used in generating the correlation distribution, overlapped with the correlation distribution. For example, the display controller 205 causes display of the gray scale image shown in FIG. 7 overlapped with the correlation distribution shown in FIG. 9A using dashed lines. By adopted such a constitution, a worker or administrator can easily grasp in which rebar there is the possibility that deterioration has occurred by viewing the display.

The constitution may be made such that, when some location in the correlation distribution is selected, the display controller 205 causes display of information regarding the selected location. The selected location may be any location within the correlation distribution. In this case, the information regarding the selected location is, for example, information of whether or not the correlation of the region that includes the selected location exceeds a threshold, the correlation of the region that includes the selected location, or information indicating an area of the region including the selected location in the gray scale image. The display controller 205 may cause a pop-up display of information regarding the selected location, or may use another display method. By adopting a constitution such as this, the structure evaluation apparatus 20 can present more detailed information.

The display controller 205 may operate as an output controller that controls the output and outputs a correlation distribution generated base on the evaluation results and the gray scale image. In this case, an output includes the display 206, a communicator, or a printer. If the output is a communicator, the output controller controls the communicator to transmit the correlation distribution to another device. If the output is a printer, the output controller controls the printer to print the correlation distribution. The structure evaluation apparatus 20 may have a part or all of the display 206, the communicator, and the printer as the output and may execute the above-noted operations.

In the present embodiment, the constitution shown has been one in which the structure evaluation apparatus 20 calculates the correlation using the gray scale image f(x, y)

of one region (target region) that includes a rebar as the reference distribution. However, as shown in FIG. 7, the reinforced concrete 1 includes the main rebars 45 and force-distributing rebars 46. For that reason, when the structure evaluation apparatus 20 calculates the correlation using the distribution of a region that includes the one rebar (for example, the main rebar 45) as the reference distribution, the correlation with a region that includes the main rebar 45 and the force-distributing rebar 46 is reduced, and in such cases the accurate correlation cannot be calculated.

Given this, the structure evaluation apparatus 20 may be constituted so as to perform the following operation. Specifically, if a distribution of a certain region that includes one rebar is the reference distribution, the structure evaluation apparatus 20 calculates the degree of similarity with a distribution of a certain region that includes one rebar of the distribution of a certain region in the vicinity of a rebar within the gray scale image. If a distribution of a certain region that includes intersecting rebars (the main rebar 45 and the force-distribution rebar 46) as the reference distribution, the structure evaluation apparatus 20 calculates the degree of similarity with a distribution of a certain region that includes intersecting rebars of the distribution of a certain region in the vicinity of a rebar. Adopting a constitution such as this enables a more accurate calculation of the correlation.

According to at least one embodiment described above, the structure evaluation apparatus 20 has an acquisitor 201 and an evaluator 204. The acquisitor 201 acquires a gray scale image. The evaluator 204 calculates similarity, with reference to a reference region including the material in the gray scale image, of other regions including the material than the reference region in the gray scale image. This constitution enables a stable evaluation of the damageless of reinforced concrete.

While certain embodiments of the present inventions have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A structure evaluation apparatus comprising:
    an acquisitor configured to acquire intensity distribution that represents a distribution of strength of a reflected wave obtained by an electromagnetic radar scan to a reinforced concrete which comprises concrete and a material, the material being a material other than concrete; and
    an evaluator configured to calculate a correlation value, the correlation value being based on at least one reference region image including the material in the intensity distribution and based on other regions images including the material that are not the reference region image,
    wherein the at least one reference region image is an image of a region that is considered sound,
    wherein the at least one reference region image includes a first reference region and a second reference region, each of the first reference region and a second reference region being considered sound,
    wherein the first reference region includes the material without any intersection between the material and other material in the intensity distribution,
    wherein the second reference region includes the material and is the material intersecting with another material in the intensity distribution,
    wherein the evaluator calculates correlation value of first regions that are selected in the other regions with reference to the first reference region,
    wherein each of the first regions includes the material without any intersection between the material and other material,
    wherein the evaluator calculates correlation value of second regions that are selected in the other regions with reference to the second reference region,
    wherein each of the second regions includes the material and is the material intersecting with another material,
    wherein the evaluator evaluates whether or not each of the first regions is sound based on the calculated correlation value of each of the first regions, and
    wherein the evaluator evaluates whether or not each of the second regions is sound based on the calculated correlation value of each of the second regions.

2. The structure evaluation apparatus according to claim 1, further comprising:
    an output configured to output a correlation distribution responded on the correlation value of each of the first regions and the correlation value of each of the second regions.

3. The structure evaluation apparatus according to claim 2, further comprising:
    a display controller that displays information regarding a selected location selected within the correlation distribution.

4. The structure evaluation apparatus according to claim 1, wherein the material is different in permittivity from concrete.

5. The structure evaluation apparatus according to claim 4, wherein the material is a rebar.

6. A structure evaluation system comprising:
    an electromagnetic radar apparatus that generates intensity distribution by scanning, with electromagnetic radar, reinforced concrete that comprises concrete and a material, the material being a material other than concrete; and
    a structure evaluation apparatus that comprises an acquisitor that acquires the intensity distribution from the electromagnetic radar apparatus, and an evaluator that calculates a correlation a value, the correlation value being based on at least one reference region image including the material in the distribution and based on other regions images including the material that are not the reference region image,
    wherein the at least one reference region image is an image of a region that is considered sound,
    wherein the at least one reference region image includes a first reference region and a second reference region, each of the first reference region and a second reference region being considered sound,
    wherein the first reference region includes the material without any intersection between the material and other material in the intensity distribution,
    wherein the second reference region includes the material and is the material intersecting with another material in the intensity distribution, wherein the evaluator calculates correlation value of first regions that are selected in the other regions with reference to the first reference region, wherein each of the first regions includes the material without any intersection between the material and other material, wherein the evaluator calculates correlation value of second regions that are selected in the other regions with reference to the second reference region, wherein each of the second regions includes the material and is the material intersecting with another material, wherein the evaluator evaluates whether or not each of the first regions is sound based on the calculated correlation value of each of the first regions, and wherein the evaluator evaluates whether or not each of the second regions is sound based on the calculated correlation value of each of the second regions.

7. A structure evaluation method comprising:

acquiring intensity distribution that represents a distribution of strength of a reflected wave obtained by an electromagnetic radar scan to a reinforced concrete which comprises concrete and a material, the material being a material other than concrete; and calculating a correlation a value, the correlation value being based on at least one reference region image including the material in the intensity distribution and based on other regions images including the material that are not the reference region image, wherein the at least one reference region image is an image of a region that is considered sound, wherein the at least one reference region image includes a first reference region and a second reference region, each of the first reference region and a second reference region being considered sound, wherein the first reference region includes the material without any intersection between the material and other material in the intensity distribution, wherein the second reference region includes the material and is the material intersecting with another material in the intensity distribution, wherein the evaluator calculates correlation value of first regions that are selected in the other regions with reference to the first reference region, wherein each of the first regions includes the material without any intersection between the material and other material, wherein the evaluator calculates correlation value of second regions that are selected in the other regions with reference to the second reference region, wherein each of the second regions includes the material and is the material intersecting with another material, wherein the evaluator evaluates whether or not each of the first regions is sound based on the calculated correlation value of each of the first regions, and wherein the evaluator evaluates whether or not each of the second regions is sound based on the calculated correlation value of each of the second regions.

* * * * *